United States Patent
Park et al.

(10) Patent No.: US 11,844,611 B2
(45) Date of Patent: Dec. 19, 2023

(54) ANTIOXIDANT SENSOR, ANTIOXIDANT SIGNAL OBTAINING METHOD, AND ANTIOXIDANT LEVEL DETERMINING METHOD

(71) Applicant: SAMSUNG ELECTRONICS CO., LTD., Suwon-si (KR)

(72) Inventors: Jin Young Park, Hwaseong-si (KR); Sung Mo Ahn, Yongin-si (KR); Kun Sun Eom, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 219 days.

(21) Appl. No.: 16/521,988

(22) Filed: Jul. 25, 2019

(65) Prior Publication Data

US 2020/0029873 A1 Jan. 30, 2020

(30) Foreign Application Priority Data

Jul. 27, 2018 (KR) .................. 10-2018-0088097

(51) Int. Cl.
*A61B 5/1455* (2006.01)
*A61B 5/145* (2006.01)
*A61B 5/00* (2006.01)

(52) U.S. Cl.
CPC ........ *A61B 5/14546* (2013.01); *A61B 5/0053* (2013.01); *A61B 5/1455* (2013.01); *A61B 5/486* (2013.01); *A61B 5/7278* (2013.01)

(58) Field of Classification Search
CPC . A61B 5/14546; A61B 5/0053; A61B 5/1455; A61B 5/486; A61B 5/7278;
(Continued)

(56) References Cited

U.S. PATENT DOCUMENTS 6,205,354 B1  3/2001  Gellermann et al.
7,558,619 B2  7/2009  Ferguson et al.
(Continued)

FOREIGN PATENT DOCUMENTS

EP  1402820 B1 * 11/2012  .......... A61B 5/1455
JP  2000074923 A  3/2000
(Continued)

OTHER PUBLICATIONS

I. A. Nakhaeva et al. "The effect of an External Mechanical Compression on in vivo Optical Properties of Human Skin" Optics and Spectroscopy, vol. 117, No. 3, Sep. 23, 2014, (pp. 506-512) XP035396255.

(Continued)

*Primary Examiner* — Chu Chuan Liu
(74) *Attorney, Agent, or Firm* — Sughrue Mion, PLLC

(57) ABSTRACT

An antioxidant sensor includes a first light source configured to emit light having a first wavelength onto an object; a second light source configured to emit light having a second wavelength onto the object; a third light source configured to emit light having a third wavelength onto the object, the first wavelength, the second wavelength, and the third wavelength being different from each other; a light receiver configured to receive light reflected or scattered from the object; and a processor configured to obtain a hemoglobin index by driving the first light source and the second light source, and to obtain an antioxidant signal of the object by driving the third light source based on the obtained hemoglobin index satisfying a condition.

21 Claims, 18 Drawing Sheets

(58) Field of Classification Search
CPC ............ A61B 5/14551; A61B 5/14552; A61B 5/14532; A61B 5/0075
See application file for complete search history.

(56) References Cited

U.S. PATENT DOCUMENTS

| | | | |
|---|---|---|---|
| 8,231,914 B2 | 7/2012 | McAnalley et al. | |
| 8,260,402 B2 | 9/2012 | Ermakov et al. | |
| 9,194,858 B2 | 11/2015 | Pezzaniti | |
| 9,402,546 B2 | 8/2016 | Segman | |
| 9,814,417 B2 | 11/2017 | Sharifzadeh et al. | |
| 2003/0032892 A1* | 2/2003 | Erlach | A61B 5/4839 600/547 |
| 2008/0221415 A1 | 9/2008 | Sweeney | |
| 2009/0306521 A1* | 12/2009 | Ermakov | A61B 5/0075 600/477 |
| 2011/0193704 A1* | 8/2011 | Harper | A61B 5/14 340/573.1 |
| 2012/0330164 A1 | 12/2012 | Ermakov et al. | |
| 2013/0289414 A1 | 10/2013 | Adibnazari et al. | |
| 2014/0058224 A1 | 2/2014 | Gellermann et al. | |
| 2014/0378779 A1* | 12/2014 | Freeman | A61B 5/1032 600/301 |
| 2015/0287191 A1 | 10/2015 | Koruga et al. | |
| 2016/0334332 A1 | 11/2016 | Magnussen et al. | |
| 2017/0340273 A1 | 11/2017 | Morita | |

FOREIGN PATENT DOCUMENTS

| | | | | |
|---|---|---|---|---|
| JP | 2007-286022 A | | 11/2007 | |
| KR | 20080072158 A | * | 8/2008 | ......... A61B 5/14532 |
| KR | 1020110038020 A | | 4/2011 | |
| WO | WO-2005011479 A2 | * | 2/2005 | ............ A61B 5/0225 |

OTHER PUBLICATIONS

Communication dated Dec. 5, 2019, from the European Patent Office in counterpart European Application No. 19188560.7.
Korean Office Action dated Nov. 23, 2022 issued by the Korean Patent Office in App No. 10-2018-0088097.

* cited by examiner

ANTIOXIDANT SENSOR, ANTIOXIDANT SIGNAL OBTAINING METHOD, AND ANTIOXIDANT LEVEL DETERMINING METHOD

CROSS-REFERENCE TO RELATED APPLICATION(S)

This application claims priority from Korean Patent Application No. 10-2018-0088097, filed on Jul. 27, 2018, in the Korean Intellectual Property Office, the entire disclosure of which is herein incorporated by reference for all purposes.

BACKGROUND

1. Field

The apparatuses and methods consistent with the example embodiments relate to an apparatus and a method for obtaining an antioxidant signal and an antioxidant level in a non-invasive manner.

2. Description of the Related Art

Reactive oxygen species such as white blood cells are an important part of the biological defense mechanisms, that protect the body, e.g., against infections. However, it has been known that excessive production of reactive oxygen species in the body may lead to various diseases in tissues.

Common factors that cause the reactive oxygen species include stress, alcohol, peroxides, medicine, and the like. The reactive oxygen species produced by these factors may cause cranial nerve diseases, circulatory diseases, cancer, digestive tract diseases, liver diseases, arteriosclerosis, renal diseases, diabetes, aging, and the like.

Our bodies have a series of antioxidant defense systems to protect against oxygen toxicity. For normal operation of the systems, it is very important to have sufficient amounts of antioxidants such as vitamin E, vitamin C, carotenoid, flavonoid, and the like. As it is important to consume sufficient amounts of foods that are rich in antioxidants for an effective antioxidant action, there is a need for an apparatus for easily identifying the amount of antioxidants in the body.

SUMMARY

One or more example embodiments provide an antioxidant sensor, a method of obtaining an antioxidant signal, and a method of determining an antioxidant level in a non-invasive manner.

According to an aspect of an example embodiment, provided is an antioxidant sensor includes a first light source configured to emit light having a first wavelength onto an object; a second light source configured to emit light having a second wavelength onto the object; a third light source configured to emit light having a third wavelength onto the object, the first wavelength, the second wavelength, and the third wavelength being different from each other; a light receiver configured to receive light reflected or scattered from the object; and a processor configured to obtain a hemoglobin index by driving the first light source and the second light source, and to obtain an antioxidant signal of the object by driving the third light source based on the obtained hemoglobin index satisfying a condition.

The antioxidant signal is a signal associated with carotenoid.

The processor may be further configured to: obtain a hemoglobin signal of the object by driving the first light source; obtain a base signal by driving the second light source; and obtain the hemoglobin index by normalizing the hemoglobin signal based on the base signal.

The processor may be further configured to obtain the hemoglobin index by subtracting the base signal from the hemoglobin signal or by dividing the hemoglobin signal by the base signal.

The first wavelength may be a green wavelength; and the second wavelength may be a red wavelength.

The obtained hemoglobin index may be based on pressure applied to the object.

In response to the obtained hemoglobin index being lower than a predetermined threshold value, the processor may be further configured to obtain the antioxidant signal by driving the third light source.

The processor may be further configured to preprocess the antioxidant signal based on a hemoglobin signal obtained by driving the first light source.

The processor may be further configured to normalize the antioxidant signal by subtracting the hemoglobin signal from the antioxidant signal or by dividing the antioxidant signal by the hemoglobin signal.

The third wavelength may be a blue wavelength.

In response to the obtained hemoglobin index being greater than or equal to a predetermined threshold value, the processor may be further configured to generate guide information indicating to increase pressure applied to the object, and provide the guide information to a user.

The light receiver may include at least one of a photodetector or a spectrometer.

The antioxidant sensor may further include at least one light source configured to emit light having one or more wavelengths to the object, wherein the processor is further configured to, in response to the obtained hemoglobin index being lower than a predetermined threshold value, obtain the antioxidant signal by driving the third light source, obtain at least one preprocessing signal by driving the at least one light source, and preprocess the antioxidant signal based on the at least one preprocessing signal.

The one or more wavelengths may include a green wavelength or a wavelength that is a blue wavelength.

The processor may be further configured to determine an antioxidant level by analyzing the antioxidant signal.

In response to the antioxidant level being lower than a predetermined threshold level, the processor may be configured to generate recommendation information indicating to increase the antioxidant level and provide the recommendation information to a user.

According to an aspect of an example embodiment, provided is an antioxidant sensor, including: a spectrum obtainer configured to obtain a skin spectrum of an object; and a processor configured to obtain a hemoglobin index based on the skin spectrum, and to determine an antioxidant level of the object based on to the obtained hemoglobin index.

The spectrum obtainer may include: a plurality of light sources configured to emit light having different wavelengths onto the object; a photodetector configured to receive light reflected or scattered from the object; and a spectrum reconstructor configured to reconstruct the skin spectrum based on the received light.

The spectrum obtainer may include: a plurality of light sources configured to emit light having different wavelengths onto the object; and a spectrometer configured to generate the skin spectrum by separating the light reflected or scattered from the object.

The spectrum obtainer may include: a light source configured to emit white light onto the object; and a spectrometer configured to generate the skin spectrum by separating the light reflected or scattered from the object.

The processor may be further configured to extract absorbance of a first wavelength and absorbance of a second wavelength from the skin spectrum, and obtains the hemoglobin index by normalizing the absorbance of the first wavelength based on the absorbance of the second wavelength.

The processor may be further configured to obtain the hemoglobin index by subtracting the absorbance of the second wavelength from the absorbance of the first wavelength, or by dividing the absorbance of the first wavelength by the absorbance of the second wavelength The first wavelength may be a green wavelength; and the second wavelength may be a red wavelength.

The obtained hemoglobin index is based on pressure applied to the object.

In response to the obtained hemoglobin index being lower than a predetermined threshold value, the processor may be further configured to extract absorbance of a third wavelength from the skin spectrum, and determine the antioxidant level of the object based on the extracted absorbance of the third wavelength.

The processor may be further configured to extract preprocessing absorbance of at least one wavelength from the skin spectrum, and preprocess the absorbance of the third wavelength based on the preprocessing absorbance.

The third wavelength may be a blue wavelength; and the at least one wavelength may be the blue wavelength or a green wavelength.

The processor may be further configured to, in response to the obtained hemoglobin index being greater than or equal to a predetermined threshold value, generate guide information indicating to increase pressure applied to the object, and provide the guide information to a user.

The processor may be further configured to, in response to the obtained hemoglobin index being greater than or equal to a predetermined threshold value, extract absorbance of a third wavelength from the skin spectrum, and correct the extracted absorbance of the third wavelength based on the hemoglobin index.

The processor may be further configured to correct the absorbance of the third wavelength by using a correction model which defines a relationship between the hemoglobin index and the absorbance of the third wavelength.

In response to the antioxidant level being lower than a predetermined threshold level, the processor may be configured to generate recommendation information indicating to increase the antioxidant level and provide the recommendation information to a user.

According to an aspect of an example embodiment, provided is a method of obtaining an antioxidant signal, including: obtaining a hemoglobin index by driving, with respect to an object, a first light source configured to emit light having a first wavelength and a second light source configured to emit light having a second wavelength; and obtaining an antioxidant signal of the object based on the obtained hemoglobin index satisfying a condition.

The obtaining of the hemoglobin index may include: obtaining a hemoglobin signal of the object by driving the first light source; obtaining a base signal by driving the second light source; and normalizing the hemoglobin signal based on the base signal.

The normalizing may include obtaining the hemoglobin signal by subtracting the base signal from the hemoglobin signal or by dividing the hemoglobin signal by the base signal.

The first wavelength may be a green wavelength; and the second wavelength may be a red wavelength.

The obtained hemoglobin index may be based on pressure applied to the object.

The obtaining the antioxidant signal may include, in response to the obtained hemoglobin index being lower than a predetermined threshold value, obtaining the antioxidant signal by driving a third light source configured to emit light having a third wavelength.

The obtaining the antioxidant signal may include preprocessing the antioxidant signal based on a hemoglobin signal obtained by driving the first light source.

The preprocessing may include preprocessing the antioxidant signal by subtracting the hemoglobin signal from the antioxidant signal or by dividing the antioxidant signal by the hemoglobin signal.

The third wavelength may be a blue wavelength.

The obtaining the antioxidant signal may include, in response to the obtained hemoglobin index being greater than or equal to a predetermined threshold value, generating guide information indicating to increase pressure applied to the object, and providing the guide information to a user.

The obtaining the antioxidant signal may include: obtaining at least one preprocessing signal by driving at least one light source configured to emit light having one or more wavelengths; and preprocessing the antioxidant signal based on the at least one preprocessing signal.

The one or more wavelengths may include a green wavelength or a blue wavelength.

The method may include determining an antioxidant level of the object based on the antioxidant signal.

According to an aspect of an example embodiment, provided is a method of determining an antioxidant level, the method including: obtaining a skin spectrum of an object; obtaining a hemoglobin index by analyzing the skin spectrum; and determining an antioxidant level of the object based on the obtained hemoglobin index.

The obtaining the hemoglobin index may include extracting absorbance of a first wavelength and absorbance of a second wavelength from the skin spectrum; and obtaining the hemoglobin index by normalizing the extracted absorbance of the first wavelength based on the extracted absorbance of the second wavelength.

The first wavelength may be a green wavelength and the second wavelength may be a red wavelength.

The obtained hemoglobin index may be based on pressure applied to the object.

The determining may include, in response to the obtained hemoglobin index being lower than a predetermined threshold value, extracting absorbance of a third wavelength from the skin spectrum; and determining the antioxidant level of the object based on the extracted absorbance of the third wavelength.

The third wavelength may be a blue wavelength.

The determining the antioxidant level of the object based on the extracted absorbance of the third wavelength may include extracting preprocessing absorbance of at least one wavelength from the skin spectrum; and preprocessing the absorbance of the third wavelength based on the preprocessing absorbance.

The determining the antioxidant level may include in response to the obtained hemoglobin index being greater than or equal to a predetermined threshold value, generating guide information indicating to increase pressure applied to the object, and providing the guide information to a user.

The determining the antioxidant level may include in response to the obtained hemoglobin index being greater than or equal to a predetermined threshold value, extracting absorbance of a third wavelength from the skin spectrum; correcting the extracted absorbance of the third wavelength based on the hemoglobin index; and determining the antioxidant level of the object based on the corrected absorbance of the third wavelength.

BRIEF DESCRIPTION OF THE DRAWINGS

The above and/or other aspects will be more apparent by describing certain example embodiments, taken in conjunction with the accompanying drawings.

DETAILED DESCRIPTION

Figure 1:
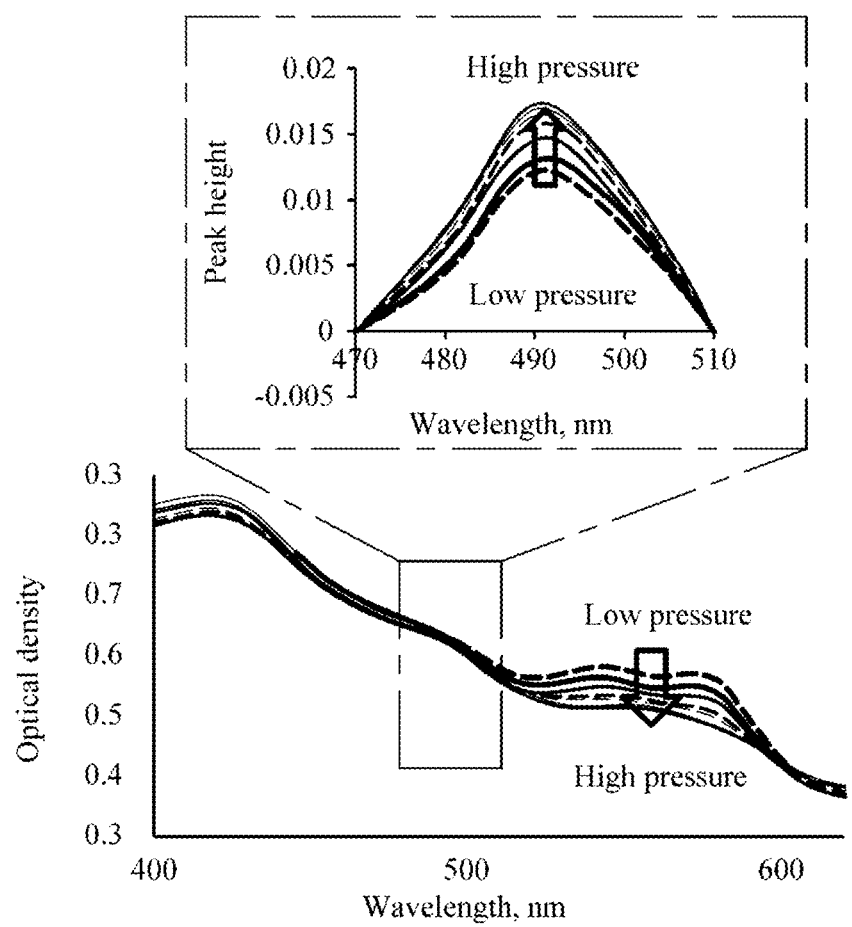
FIG. 1 is an example diagram illustrating a change in a skin optical density spectrum according to pressure applied to skin.

Hereinafter, example embodiments will be described in detail with reference to the accompanying drawings. Throughout the drawings and the detailed description, unless otherwise described, the same drawing reference numerals will be understood to refer to the same elements, features, and structures. The relative size and depiction of these elements may be exaggerated for clarity, illustration, and convenience. In the following description, a detailed description of known functions and configurations incorporated herein will be omitted when it may obscure the subject matter of the disclosure.

Process steps described herein may be performed differently from a specified order, unless a specified order is clearly stated in the context of the disclosure. That is, each step may be performed in a specified order, at substantially the same time, or in a reverse order.

Further, the terms used throughout this specification are defined in consideration of the functions according to example embodiments, and can be varied according to a purpose of a user or manager, or precedent and so on. Therefore, definitions of the terms should be made on the basis of the overall context.

It will be understood that, although the terms first, second, etc. may be used herein to describe various elements, these elements should not be limited by these terms. These terms are only used to distinguish one element from another. Any references to singular may include plural unless expressly stated otherwise. In the present specification, it should be understood that the terms, such as 'including' or 'having,' etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

Further, components that will be described in the specification are discriminated merely according to functions mainly performed by the components, That is, two or more components which will be described later can be integrated into a single component. Furthermore, a single component which will be explained later can be separated into two re components. Moreover, each component which will be described can additionally perform some or all of a function executed by another component in addition to the main function thereof. Some or all of the main function of each component which will be explained can be carried out by another component. Each component may be implemented as hardware, software, or a combination of both.

It will be understood that, the terms, such as "unit," "module," "component," "part," etc., should be understood as an element that performs at least one function or operation and that may be embodied as hardware, software, or a combination thereof. Further, a plurality of "modules" or "units" may be integrated into at least one module and implemented as at least one processor, except "modules" or "unit" that need to be implemented as specific hardware.

As used herein, expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, or all of a, b, and c.

Figure 2:
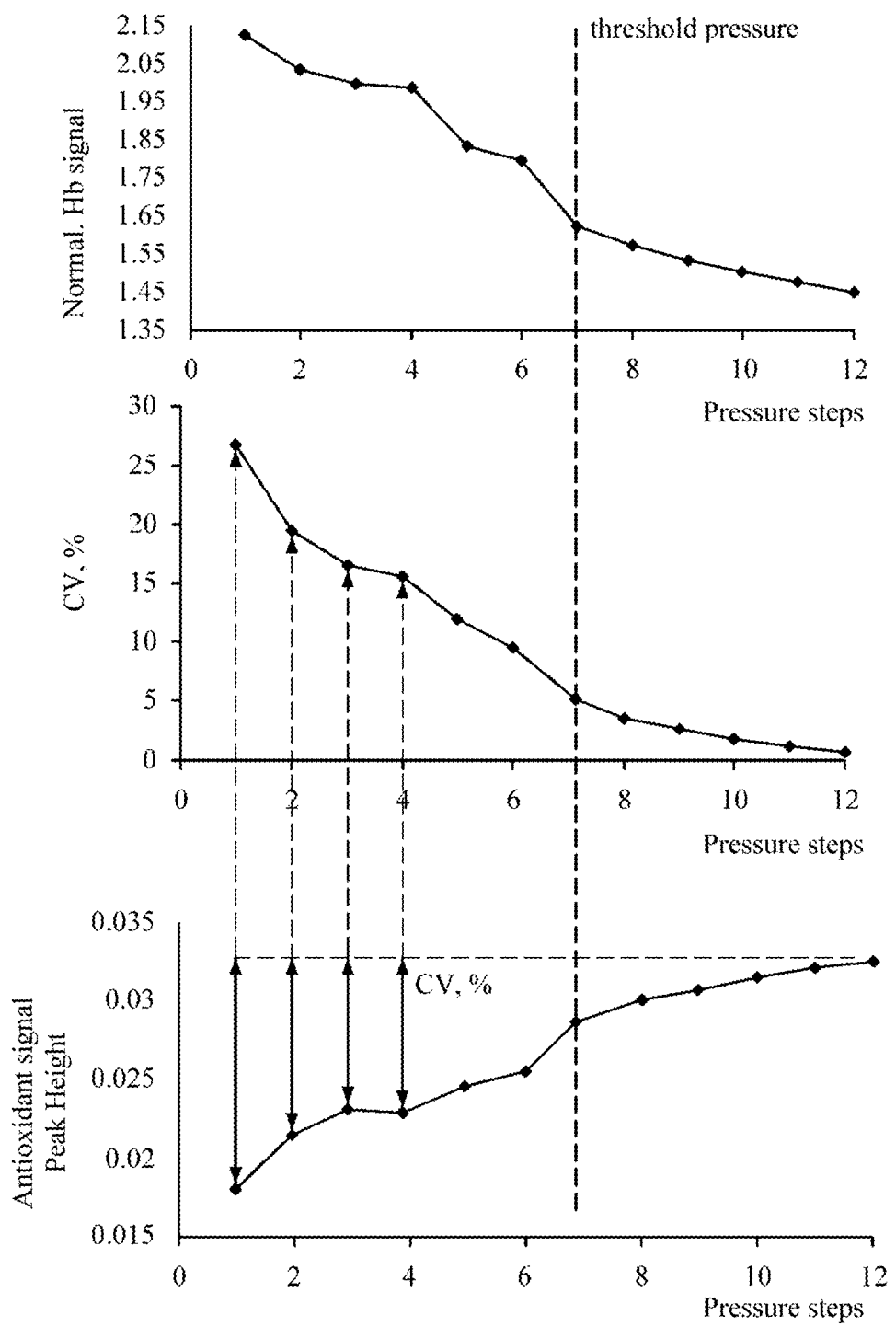
FIG. 2 is an example diagram illustrating a change in an antioxidant signal in skin according to pressure applied to skin.

FIG. 1 is an example diagram illustrating a change in a skin optical density spectrum according to pressure applied to skin, and FIG. 2 is an example diagram illustrating a change in an antioxidant signal in skin according to pressure applied to skin.

Referring to FIG. 1, it can be seen that a skin optical density spectrum is changed according to pressure applied to skin. For example, it can be seen from the example of FIG. 1 that in a wavelength band of about 520 nm to 590 nm, skin optical density decreases as pressure applied to skin increases; and in a wavelength band of 470 not to 510 nm, a peak height increases as pressure applied to skin increases. Here, the wavelength hand of 470 nm to 510 nm may be included in a wavelength band, in which an antioxidant signal is measured, i.e., an absorption band of an antioxidant substance (e.g., carotenoid); and the wavelength band of 520 nm to 590 nm may be included in a wavelength band, in which a hemoglobin signal is measured, i.e., an absorption band of hemoglobin. Further, the peak height may indicate optical density, from which interference caused by a substance other than an antioxidant substance is eliminated by a preprocessing process (e.g., baseline correction, normalization, etc.).

Referring to FIG. 2, it can be seen that as pressure applied to skin increases, a peak height of an antioxidant signal increases, and at a pressure greater than or equal to a predetermined level, an antioxidant signal is saturated and stabilized. Accordingly, it can be seen that a coefficient of variation (CV) of peak height of an antioxidant signal decreases as pressure applied to skin increases. Further, a hemoglobin signal (Normal. Hb signal) detected from skin decreases as pressure applied to skin increases, and a change trend of a hemoglobin signal according to a pressure change is similar to a change trend of a CV of an antioxidant signal according to a pressure change.

Accordingly, pressure applied to an object may be estimated by analyzing a hemoglobin signal, and an antioxidant signal may be measured by guiding a user to apply pressure, which is greater than or equal to a threshold pressure, to the object, such that an antioxidant signal having a high signal-to-noise ratio may be obtained without using a pressure sensor.

Figure 3:
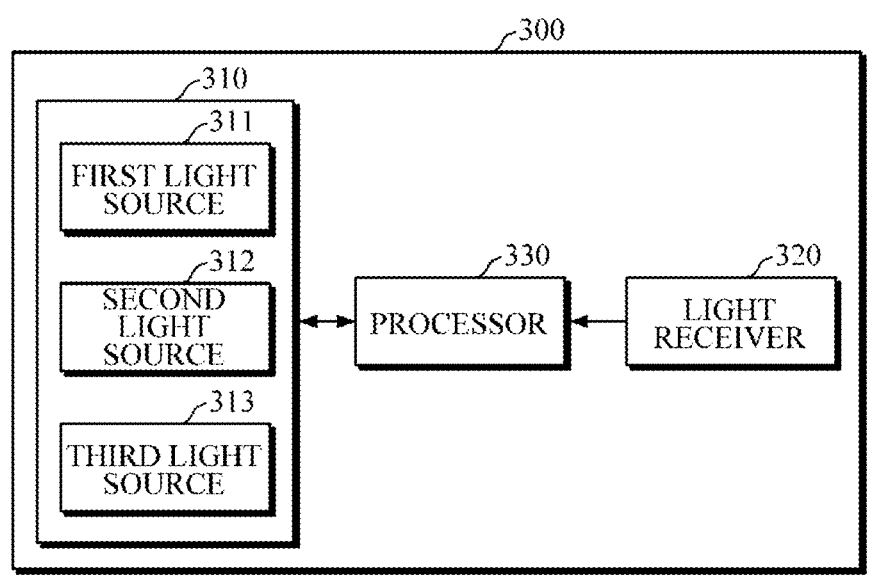
FIG. 3 is a diagram illustrating an example of an antioxidant sensor according to an example embodiment.

FIG. 3 is a diagram illustrating an example of an antioxidant sensor according to an example embodiment. The antioxidant sensor 300 of FIG. 3 is an apparatus for obtaining an antioxidant index of an object in a non-invasive manner according to an example embodiment, and may be embedded in an electronic device. Further, the antioxidant sensor 300 of FIG. 3 may be enclosed in a housing to be provided as a separate device. In this case, examples of the electronic device may include a cellular phone, a smartphone, a tablet personal computer (PC), a laptop computer, a personal digital assistant (PDA), a portable multimedia player (PMP), a navigation, an MP3 player, a digital camera, a wearable device, and the like. Examples of the wearable device may include a wristwatch-type wearable device, a wristband-type wearable device, a ring-type wearable device, a waist belt-type wearable device, a necklace-type wearable device, an ankle band-type wearable device, a thigh band-type wearable device, a forearm band-type wearable device, and the like. The electronic device is not limited to the above examples, and the wearable device is neither limited thereto.

Referring to FIG. 3, the antioxidant sensor 300 includes a light source unit 310, a light receiver 320, and a processor 330. Here, the processor 330 may include one or more processors, a memory, and a combination thereof.

The light source unit 310 may include a plurality of light sources 311 to 313 which emit light of different wavelengths onto an object. For example, the light source unit 310 may include: a first light source 311 which emits light of a first wavelength; a second light source 312 which emits light of a second wavelength; and a third light source 313 which emits light of a third wavelength. In this case, the first wavelength may be a green wavelength included in a wavelength band, in which a hemoglobin signal is measured, i.e., an absorption band of hemoglobin; the second wavelength may be a red wavelength included in a wavelength band in which a base signal is measured; and the third wavelength may be a blue wavelength included in a wavelength band, in which an antioxidant signal is measured, i.e., an absorption band of an antioxidant. Here, the base signal may be used to normalize the hemoglobin signal.

In one embodiment, each of the light sources 311, 312, and 313 may include a light emitting diode (LED), a laser diode, a fluorescent body, and the like. The light source unit 310 may further at least one optical element (e.g., mirror, etc.) for directing the light emitted by each of the light sources 311, 312, and 313 toward a desired position of an object.

The light receiver 320 may receive light reflected or scattered from the object. In one embodiment, the light receiver 320 may be used as a photodetector or a spectrometer. Here, the photodetector may receive light reflected or scattered from an object, and may the received light into an electric signal, and may include a photo diode, a photo transistor (PTr), a charge-coupled device (CCD), or the like. Further, the spectrometer may receive light reflected or scattered from an object and may separate the received light, and may include an interference spectrometer, a grating spectrometer, a prism spectrometer, and the like.

In one embodiment, the light receiver 320 may further include at least one optical element (e.g., mirror, etc.) for directing light reflected or scattered from an object toward the light receiver 320.

The processor 330 may control the overall operation of the antioxidant sensor 300.

The processor 330 may obtain a hemoglobin index by driving the first light source 311 and the second light source 312. Here, the hemoglobin index is obtained by normalizing a hemoglobin signal, and may be related to pressure applied to an object.

Specifically, the processor 330 may drive the first light source 311 to emit light of the first wavelength onto an object, and may measure a hemoglobin signal based on light that is reflected or scattered from the object and received by the light receiver 320. Further, the processor 330 may drive the second light source 312 to emit light of the second wavelength onto an object, and may measure a base signal based on light that is reflected or scattered from the object and received through the light receiver 320. In addition, the processor 330 may obtain a hemoglobin index by normalizing the hemoglobin signal based on the base signal. For example, the processor 330 may normalize the hemoglobin signal by subtracting the base signal from the hemoglobin signal or by dividing the hemoglobin signal by the base signal, and may obtain the normalized hemoglobin signal as the hemoglobin index.

The processor 330 may compare the obtained hemoglobin index with a predetermined threshold value, and may measure an antioxidant signal based on the comparison. In this case, the predetermined threshold value may be preset in consideration of pressure at which an antioxidant signal is saturated and stabilized.

In one embodiment, in response to a hemoglobin index being lower than a predetermined threshold value, the processor 330 may determine that a pressure applied to an object is sufficient to measure an antioxidant signal. Upon determination, the processor 330 may drive the third light source 313 to emit light of the third wavelength onto the object, and may measure an antioxidant signal based on light that is reflected or scattered from the object and received through the light receiver 320. Further, the processor 330 may determine an antioxidant level by analyzing the measured antioxidant signal. For example, the processor 330 may determine an antioxidant level of an object by using an antioxidant level estimation model. Here, the antioxidant level estimation model defines a relationship between an antioxidant signal and an antioxidant level, and may be pre-generated by regression analysis or machine learning and stored in an internal or an external database of the processor 330. The antioxidant level estimation model may be provided in the form of a mathematical algorithm or a matching table, but is not limited thereto.

Before determining the antioxidant level of an object, the processor 330 may preprocess the measured antioxidant signal. For example, the processor 330 may normalize the antioxidant signal by subtracting the hemoglobin signal from the antioxidant signal or by dividing the antioxidant signal by the hemoglobin signal. By normalization, the processor 330 may eliminate an effect of a substance, other than an antioxidant substance, from the measured antioxidant signal.

In another example embodiment, in response to a hemoglobin index being greater than or equal to a predetermined threshold value, the processor 330 may determine that a pressure applied to an object is not sufficient to measure an antioxidant signal, and may generate guide information for guiding a user to increase pressure applied to an object and output the guide information using an output device. In this case, the output device may include all types of devices such as a visual output device (e.g., display, etc.), an audio output device (e.g., speaker, etc.), and a tactile output device (e.g., vibrator, etc.).

In response to an antioxidant level being lower than or equal to a predetermined threshold level, the processor 330 may generate information related to increasing the antioxidant level (e.g., message recommending to increase the antioxidant level) and may provide the information to a user through an output device. For example, in response to an antioxidant level being lower than or equal to a predetermined threshold level, the processor 330 may generate information, such as "eat more vegetables" "cut down on smoking," "cut down alcohol consumption," "exercise more," "reduce stress," and the like, and may provide the information to a user through an output device.

Figure 4:
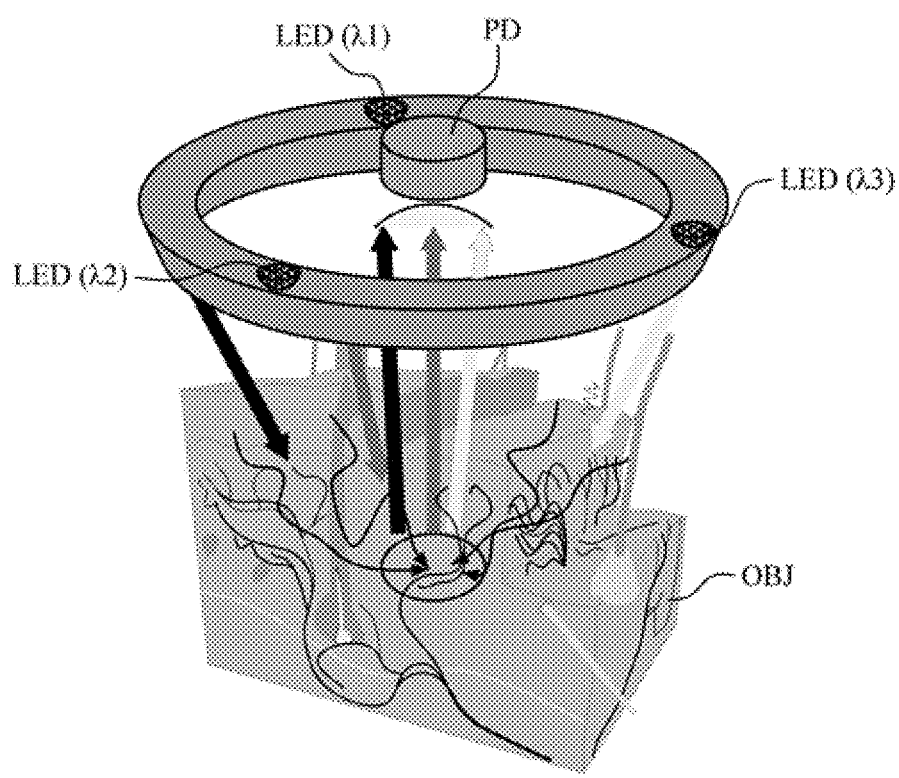
FIG. 4 is a diagram illustrating an example of a light emitting diode (LED)-photo diode (PD) structure according to an example embodiment.

FIG. 4 is a diagram illustrating an example of an LED-PD structure according to an example embodiment. The LED-PD structure of FIG. 4 may be an example of a structure of the light source unit 310 and the light receiver 320 of FIG. 3.

Referring to FIG. 4, the LED-PD structure may comprise three LEDs and one photo diode (PD). In this case, each of the LEDs may have peak wavelengths of a first wavelength $\lambda_1$, a second wavelength $\lambda_2$, and a third wavelength $\lambda_3$, respectively.

Each of the LEDs is driven sequentially according to a control signal to emit light of the predetermined peak wavelength onto an object OBJ; and the photo diode (PD) detects light returning from the object OBJ.

Figure 5:
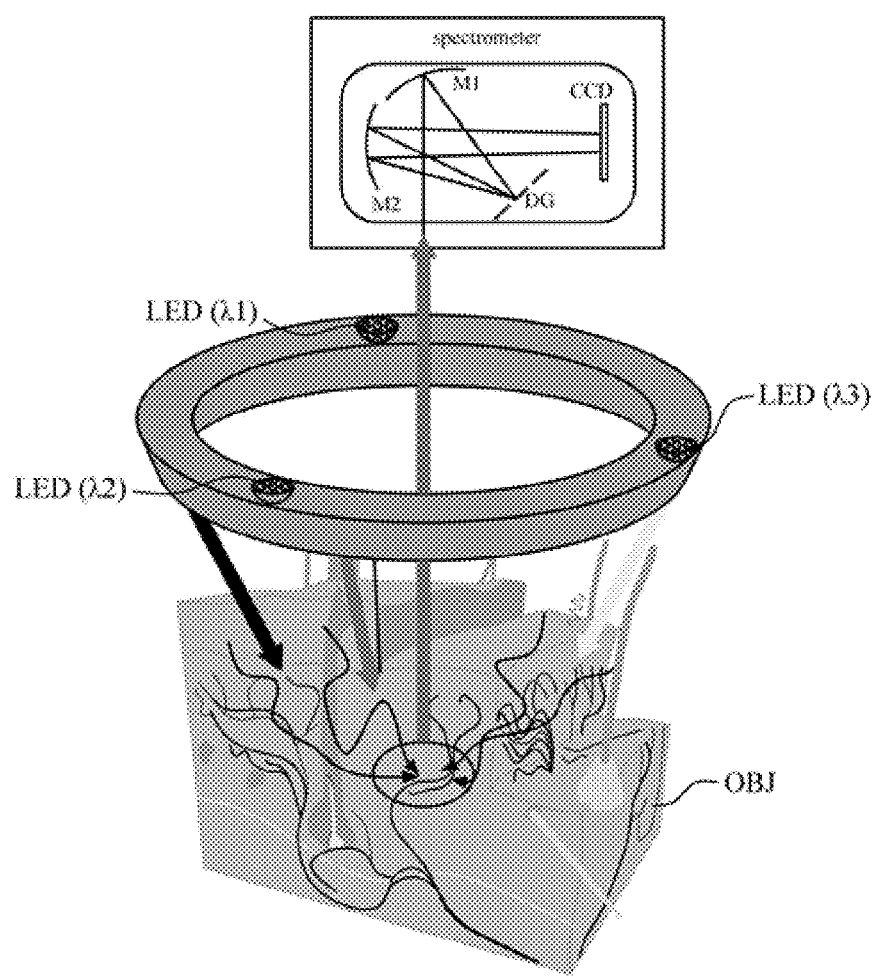
FIG. 5 is a diagram illustrating an example of an LED-spectrometer structure according to an example embodiment.

FIG. 5 is a diagram illustrating an example of an LED-spectrometer structure according to an example embodiment. The LED-spectrometer structure of FIG. 5 may be an example of a structure of the light source unit 310 and the light receiver 320 of FIG. 3.

Referring to FIG. 5, the LED-spectrometer structure may comprise three LEDs and one spectrometer. In this case, each the LEDs may have peak wavelengths of a first wavelength $\lambda_1$, a second wavelength $\lambda_2$, and a third wavelength $\lambda_3$, respectively.

Each of the LEDs is driven sequentially according to a control signal to emit light of the predetermined peak wavelength onto an object OBJ; and the spectrometer receives light returning from the object OBJ, and generates a spectrum by separating the received light. The spectrometer may include various optical elements, such as a diffraction grating, a prism, a hologram filter, a dielectric lens, or a combination thereof.

Figure 6:
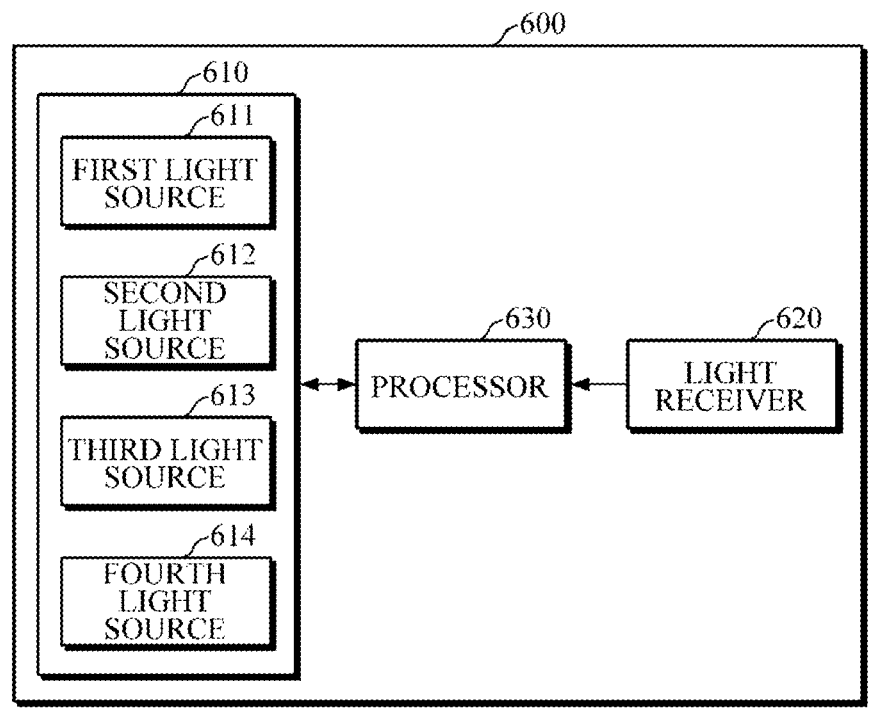
FIG. 6 is a diagram illustrating an example of an antioxidant sensor according to an example embodiment.

FIG. 6 is a diagram illustrating an example of an antioxidant sensor according to an example embodiment. An antioxidant sensor 600 of FIG. 6 is an apparatus for obtaining an antioxidant index of an object in a non-invasive manner, and may be embedded in an electronic device. Further, the antioxidant sensor 600 of FIG. 6 may be enclosed in a housing to be provided as a separate device. In this case, examples of the electronic device may include a cellular phone, a smartphone, a tablet PC, a laptop computer, a personal digital assistant (PDA), a portable multimedia player (PMP), a navigation, an MP3 player, a digital camera, a wearable device, and the like; and examples of the wearable device may include a wristwatch-type wearable device, a wristband-type wearable device, a ring-type wearable device, a waist belt-type wearable device, a necklace-type wearable device, an ankle band-type wearable device, a thigh band-type wearable device, a forearm band-type wearable device, and the like. However, the electronic device is not limited to the above examples, and the wearable device is neither limited thereto.

Referring to FIG. 6, the antioxidant sensor 600 includes a light source unit 610, a light receiver 620, and a processor 630. Here, the processor 630 may comprise one or more processors, a memory, and a combination thereof. The light receiver 620 functions similarly to the light receiver 320 of FIG. 3 described above, such that detailed description thereof will be omitted.

The light source unit 610 may include: a first light source 611 which emits light of a first wavelength; a second light source 612 which emits light of a second wavelength; a third light source 613 which emits light of a third wavelength; and a fourth light source 614 which emits light of a fourth wavelength. Here, the first light source 611, the second light source 612, and the third light source 613 may be the same or similar to the first light source 311, the second light source 312, and the third light source 313 of FIG. 3 described above, such that detailed description thereof will be omitted.

The fourth light source 614 may be a light source for obtaining a signal which is used for preprocessing an antioxidant signal measured by driving the third light source 163. Hereinafter, the signal which is used for preprocessing the antioxidant signal may be referred to as a preprocessing signal. The fourth wavelength may be a wavelength different from the first wavelength and the third wavelength. For example, the fourth wavelength may be a green wavelength having a wavelength different from the first wavelength or a blue wavelength having a wavelength different from the third wavelength. Also, the fourth light source 614 may emit light having different wavelengths.

The processor 630 may control the overall operation of the antioxidant sensor 600.

The processor 630 may obtain a hemoglobin index by driving the first light source 611 and the second light source 612. Specifically, the processor 630 may measure a hemoglobin signal by driving the first light source 611, and may measure a base signal by driving the second light source 612. In addition, the processor 630 may obtain a hemoglobin index by normalizing the hemoglobin signal based on the base signal. For example, the processor 630 may normalize the hemoglobin signal by subtracting the base signal from the hemoglobin signal or by dividing the hemoglobin signal by the base signal, and may obtain the normalized hemoglobin signal as the hemoglobin index.

The processor 630 may compare the obtained hemoglobin index with a predetermined threshold value, and may measure an antioxidant signal based on the comparison.

In one embodiment, in response to a hemoglobin index being lower than a predetermined threshold value, the processor 630 may drive the third light source 613 to emit light of the third wavelength onto an object, and may measure an antioxidant signal based on light that is reflected or scattered from the object and received through the light receiver 620. In addition, the processor 630 may drive the fourth light source 614 to emit light of the fourth wavelength onto the object, and may measure a preprocessing signal based on light that is reflected or scattered from the object and received through the light receiver 620. Further, the processor 630 may preprocess the antioxidant signal by using the preprocessing signal. For example, the processor 630 may normalize the antioxidant signal by subtracting the preprocessing signal from the antioxidant signal or by dividing the antioxidant signal by the preprocessing signal. By normalization, the processor 630 may eliminate an effect of a substance, other than an antioxidant substance, from the measured antioxidant signal. In addition, the processor 630 may determine an antioxidant level of an object by analyzing the preprocessed antioxidant signal. For example, the processor 630 may determine an antioxidant level of an object by using an antioxidant level estimation model.

In another example embodiment, in response to a hemoglobin index being greater than or equal to a predetermined threshold value, the processor 630 may generate guide information for guiding a user to increase pressure applied to an object and may provide the guide information to a user through an output device.

In response to an antioxidant level being lower than or equal to a predetermined threshold level, the processor 630 may generate recommendation information (e.g., message) to increase the antioxidant level and may provide the recommendation information to a user through an output device. For example, in response to an antioxidant level being lower than or equal to a predetermined threshold level, the processor 630 may generate recommendation information, indicating, for example, "eat more vegetables," "cut down on smoking," "cut down on alcohol consumption," "exercise more," "reduce stress," and the like, and may provide the recommendation information to a user through an output device.

While FIG. 6 illustrates an example of obtaining a preprocessing signal by using one light source 614, but the disclosure is not limited thereto. That is, the antioxidant sensor 600 may include a plurality of light sources for obtaining one or more preprocessing signals, in which the plurality of light sources may emit light of different wavelengths such as wavelengths of a green wavelength or a blue wavelength. In this case, the processor 630 may drive each of the light sources to measure a plurality of preprocessing signals, and may preprocess the antioxidant signal by using the plurality of preprocessing signals. For example, the processor 630 may preprocess the antioxidant signal by performing baseline correction based on the plurality of preprocessing signals.

Figure 7:
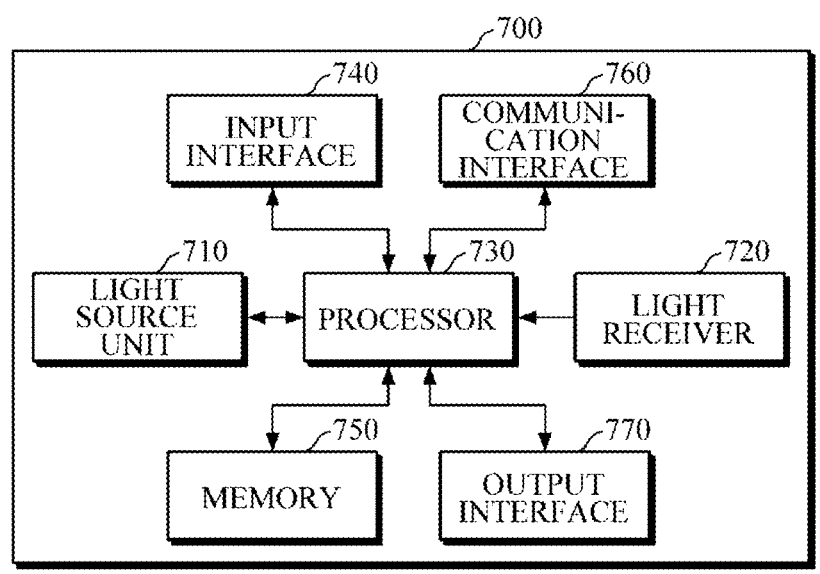
FIG. 7 is a diagram illustrating an example of an antioxidant sensor according to an example embodiment.

FIG. 7 is a diagram illustrating an example of an antioxidant sensor according to an example embodiment. An antioxidant sensor 700 of FIG. 7 is an apparatus for obtaining an antioxidant index of an object in a non-invasive manner, and may be embedded in an electronic device. Further, the antioxidant sensor 700 of FIG. 7 may be enclosed in a housing to be provided as a separate device. In this case, examples of the electronic device may include a cellular phone, a smartphone, a tablet PC, a laptop computer, a personal digital assistant (PDA), a portable multimedia player (PMP), a navigation, an MP3 player, a digital camera, a wearable device, and the like; and examples of the wearable device may include a wristwatch-type wearable device, a wristband-type wearable device, a ring-type wearable device, a waist belt-type wearable device, a necklace-type wearable device, an ankle band-type wearable device, a thigh band-type wearable device, a forearm band-type wearable device, and the like. However, the electronic device is not limited to the above examples, and the wearable device is neither limited thereto.

Referring to FIG. 7, the antioxidant sensor 700 includes a light source unit 710, a light receiver 720, and a processor 730, an input interface 740, a memory 750, a communication interface 760, and an output interface 770. Here, the light source unit 710, the light receiver 720, and the processor 730 may be the same or similar to the light source units 310 and 610, the light receivers 320 and 620, and the processors 330 and 630 of FIGS. 3 and 6 respectively, such that detailed description thereof will be omitted.

The input interface 740 may receive input of various operation signals from a user. In one embodiment, the input interface 740 may include a keypad, a dome switch, a touch pad (static pressure/capacitance), a jog wheel, a jog switch, a hardware (H/W) button, and the like. Particularly, the touch pad, which forms a layer structure with a display, may be called a touch screen.

The storage part 750 may store programs or commands for operation of the antioxidant sensor 700, and may store data input to and output from the antioxidant sensor 700. Further, the storage part 750 may store data processed by the antioxidant sensor 700, and data (e.g., antioxidant level estimation model) required for data processing of the antioxidant sensor 700.

The storage part 750 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like. Further, the antioxidant sensor 700 may operate an external storage medium, such as web storage and the like, which performs a storage function of the memory 750 on the Internet.

The communication interface 760 may perform communication with an external device. For example, the communication interface 760 may transmit, to the external device, data used by the antioxidant sensor 700, processing result data of the antioxidant sensor 700, and the like; or may receive, from the external device, various data required or useful for obtaining an antioxidant signal and/or determining an antioxidant level.

In this case, the external device may be medical equipment using the data used by the antioxidant sensor 700 or the processing result data of the antioxidant sensor 700, a printer to print out results, or a display to display the results. In addition, the external device may be a digital TV, a desktop computer, a cellular phone, a smartphone, a tablet PC, a laptop computer, a personal digital assistant (PDA), a portable multimedia player (PMP), a navigation, an MP3 player, a digital camera, a wearable device, and the like, but the external device is not limited thereto.

The communication interface 760 may communicate with an external device by using Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like. However, this is merely example and is not intended to be limiting.

The output interface 770 may output the data used by the antioxidant sensor 700 or the processing result data of the antioxidant sensor 700. In one embodiment, the output interface 770 may output the data used by the antioxidant sensor 700 or the processing result data of the antioxidant sensor 700 by using at least one of an acoustic method, a visual method, and a tactile method. To this end, the output interface 770 may include a display, a speaker, a vibrator, and the like.

Figure 8:
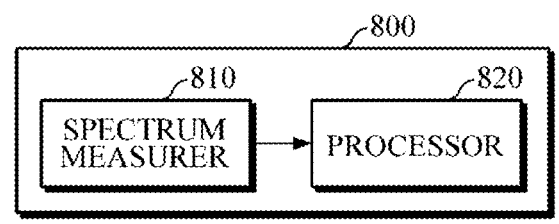
FIG. 8 is a diagram illustrating an example of an antioxidant sensor according to an example embodiment.

FIG. 8 is a diagram illustrating an example of an antioxidant sensor according to an example embodiment. An antioxidant sensor 800 of FIG. 8 is an apparatus for obtaining an antioxidant index of an object in a non-invasive manner, and may be embedded in an electronic device. Further, the antioxidant sensor 800 of FIG. 8 may be enclosed in a housing to be provided as a separate device. In this case, examples of the electronic device may include a cellular phone, a smartphone, a tablet PC, a laptop computer, a personal digital assistant (PDA), a portable multimedia player (PMP), a navigation, an MP3 player, a digital camera, a wearable device, and the like; and examples of the wearable device may include a wristwatch-type wearable device, a wristband-type wearable device, a ring-type wearable device, a waist belt-type wearable device, a necklace-type wearable device, an ankle band-type wearable device, a thigh band-type wearable device, a forearm band-type wearable device, and the like. However, the electronic device is not limited to the above examples, and the wearable device is neither limited thereto.

Referring to FIG. 8, the antioxidant sensor 800 includes a spectrum measurer 810 and a processor 820. Here, the processor 820 may comprise one or more processors, a memory, and a combination thereof.

The spectrum measurer (or spectrum obtainer) 810 may measure a skin spectrum of an object. In this case, the skin spectrum may be an absorption spectrum of skin. The spectrum measurer 810 will be described in detail later with reference to FIGS. 9 and 10.

The processor 820 may control the overall operation of the antioxidant sensor 800.

The processor 820 may obtain a hemoglobin index by analyzing the measured skin spectrum. Here, the hemoglobin index is obtained by normalizing a hemoglobin signal, and may be related to pressure applied to an object. In one embodiment, the processor 820 may extract absorbance of a first wavelength corresponding to a hemoglobin signal, and absorbance of a second wavelength corresponding to a base signal, from the measured skin spectrum; and may obtain a hemoglobin index by normalizing the absorbance of the first wavelength based on the absorbance of the second wavelength. For example, the processor 820 may normalize a hemoglobin signal by subtracting the absorbance of the second wavelength from the absorbance of the first wavelength, or by dividing the absorbance of the first wavelength by the absorbance of the second wavelength, and may obtain the normalized hemoglobin signal as a hemoglobin index. In this case, the first wavelength may be a green wavelength included in a wavelength band, in which a hemoglobin signal is measured, i.e., an absorption band of hemoglobin; and the second wavelength may be a red wavelength included in a wavelength band, in which a base signal is measured.

The processor 820 may compare the obtained hemoglobin index with a predetermined threshold value, and may determine an antioxidant level of an object based on the comparison. In this case, the predetermined threshold value may be preset in consideration of pressure at which an antioxidant signal is saturated and stabilized.

In one embodiment, in response to a hemoglobin index being lower than a predetermined threshold value, the processor 820 may determine that a pressure applied to an object is sufficient to measure an antioxidant signal. Upon determination, the processor 820 may extract absorbance of a third wavelength, corresponding to an antioxidant signal, from the skin spectrum, and may determine an antioxidant level of an object by analyzing the extracted absorbance of the third wavelength. In this case, the third wavelength may be a blue wavelength included in a wavelength band, in which an antioxidant signal is measured, i.e., an absorption band of an antioxidant substance (e.g., carotenoid). For example, the processor 820 may determine an antioxidant level of an object by using an antioxidant level estimation model. Here, the antioxidant level estimation model defines a relationship between an antioxidant signal and an antioxidant level, and may be pre-generated by regression analysis or machine learning and stored in an internal or an external database of the processor 820. The antioxidant level estimation model may be built in the form of a mathematical algorithm or a matching table, but is not limited thereto.

Before determining the antioxidant level of an object, the processor 820 may preprocess the absorbance of the third wavelength. In one embodiment, the processor 820 may extract preprocessing absorbance of at least one wavelength, corresponding to a preprocessing signal, from the skin spectrum, and may preprocess the absorbance of the third wavelength based on the extracted preprocessing absorbance. For example, the processor 820 may extract the preprocessing absorbance from one or more wavelengths, and may preprocess the absorbance of the third wavelength by performing normalization or baseline correction of the absorbance of the third wavelength based on the extracted preprocessing absorbance. In this manner, the processor 820 may eliminate an effect of a substance, other than an antioxidant substance, from the absorbance of the third wavelength. In this case, the one or more wavelengths, from which the preprocessing absorbance is extracted, may be a blue wavelength or a green wavelength.

In another example embodiment, in response to a hemoglobin index being greater than or equal to a predetermined threshold value, the processor 820 may determine that a pressure applied to an object is not sufficient to measure an antioxidant signal, and may generate guide information for guiding a user to increase pressure applied to an object and output the information using an output device. In this case, the output device may include all types of devices such as a visual output device (e.g., display, etc.), an audio output device (e.g., speaker, etc.), and a tactile output device (e.g., vibrator, etc.).

In yet another example embodiment, in response to a hemoglobin index being greater than or equal to a predetermined threshold value, the processor 820 may extract absorbance of the third wavelength, corresponding to an antioxidant signal, from the skin spectrum, and may correct the extracted absorbance of the third wavelength according to a hemoglobin index. For example, the processor 820 may correct the absorbance of the third wavelength by using a correction model. Here, the correction model defines a relationship between the absorbance of the third wavelength and the hemoglobin index, and may be pre-generated by regression analysis or machine learning and stored in an internal or an external database of the processor 820. The correction model may be built in the form of a mathematical algorithm or a matching table, but is not limited thereto. In this case, the processor 820 may determine an antioxidant level of an object based on the corrected absorbance of the third wavelength.

In response to an antioxidant level being lower than or equal to a predetermined threshold level, the processor 820 may generate recommendation to increase the antioxidant level and may provide the recommendation to a user through an output device. For example, in response to an antioxidant level being lower than or equal to a predetermined threshold level, the processor 820 may generate recommendation, such as "eat more vegetables," "cut down on smoking," "cut down on alcohol consumption," "exercise more," "reduce stress," and the like, and may provide the recommendation to a user through an output device.

Figure 9:
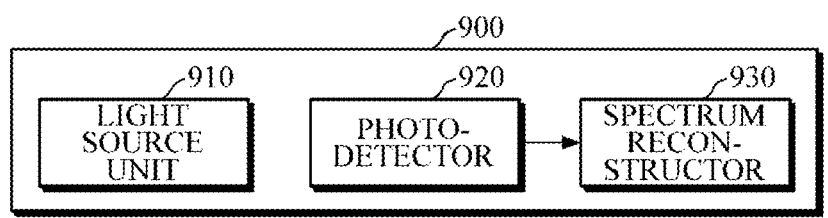
FIG. 9 is a diagram illustrating an example of a spectrum measurer according to an example embodiment.

FIG. 9 is a diagram illustrating an example of a spectrum measurer according to an example embodiment. The spectrum measurer of FIG. 9 may be an example of the spectrum measurer 810 of FIG. 8.

Referring to FIG. 9, the spectrum measurer 900 includes a light source unit 910, a photodetector 920, and a spectrum reconstructor 930.

The light source unit 920 may include a plurality of light sources which emit light of different wavelengths onto an object. Each of the light sources may emit visible light, having a blue wavelength, a green wavelength, and a red wavelength, onto an object. In one embodiment, each of the light sources may include a light emitting diode (LED), a laser diode, a fluorescent body, and the like. The light source unit 910 may further include at least one optical element (e.g., mirror, etc.) for directing the light emitted by each of the light sources toward a desired position of an object.

The photodetector 920 may receive light reflected or scattered from a user's skin, and may convert the received light into an electric signal. The photodetector 920 may include a photo diode, a photo transistor (PTr), a charge-coupled device (CCD), or the like. The photodetector 920 is not necessarily a single device, and may be formed as an array of a plurality of devices.

There may be various numbers and arrangements of light sources and photodetectors, and the number and arrangement thereof may vary according to a purpose of use of the spectrum measurer 900, the size and shape of the electronic device in which the spectrum measurer 900 is embedded, and the like.

The spectrum reconstructor 930 may obtain a skin spectrum of an object by reconstructing a spectrum using the received light and a light source spectrum. In this case, the light source spectrum may refer to a spectrum of light emitted by each light source, and information on the light source spectrum may be pre-stored in an internal or an external database.

In one embodiment, the spectrum reconstructor 930 may obtain a skin spectrum of an object using the following Equation 1.

$$R = [S_i \times S_{PD}]^{-1} \times M_{PD} \qquad \text{[Equation 1]}$$

Herein, R denotes the skin spectrum of the object, $S_i$ denotes the light source spectrum, $S_{PD}$ denotes sensitivity for each wavelength of the photodetector, and $M_{PD}$ denotes measured values of the photodetector.

Figure 10:
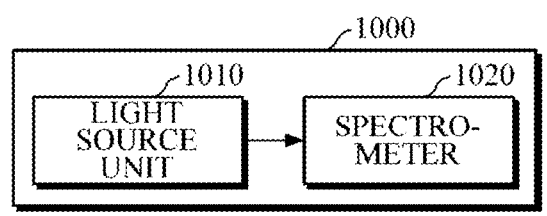
FIG. 10 is a diagram illustrating an example of a spectrum measurer according to an example embodiment.

FIG. 10 is a diagram illustrating an example of a spectrum measurer according to an example embodiment. The spectrum measurer 1000 of FIG. 10 may be an example of the spectrum measurer 810 of FIG. 8.

Referring to FIG. 10, the spectrum measurer 1000 includes a light source unit 1010 and a spectrometer 1020.

The light source unit 1010 may include one light source which emits white light onto an object, or may include a plurality of light sources which emit light of different wavelengths onto an object. The light source unit 1010 may further include at least one optical element (e.g., mirror, etc.) for directing the light emitted by each of the light sources toward a desired position of an object.

The spectrometer 1020 may receive light reflected or scattered from the object, and may generate a skin spectrum of the object by separating the received light. The spectrometer 1020 may be implemented as various types of spectrometers, such as an interference spectrometer, a grating spectrometer, a prism spectrometer, and the like, and may include various optical elements, such as a diffraction grating, a prism, a hologram filter, a dielectric lens, or a combination thereof.

Figure 11:
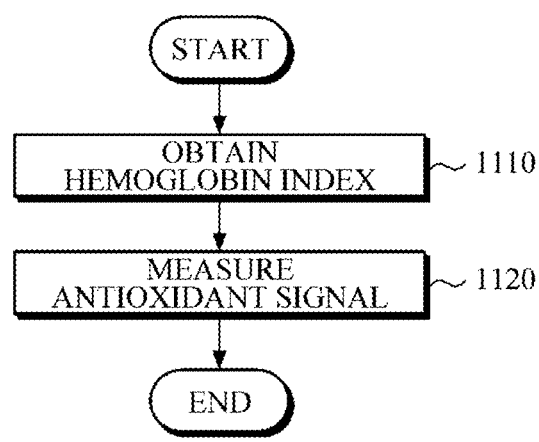
FIG. 11 is a flowchart illustrating an example of a method of obtaining an antioxidant signal according to an example embodiment.

FIG. 11 is a flowchart illustrating an example of an antioxidant signal obtaining method according to an example embodiment. The antioxidant signal obtaining method of FIG. 11 may be performed by the antioxidant sensor 300 or 600 of FIG. 3 or 6.

Referring to FIGS. 3, 6, and 11, the antioxidant sensor 300 or 600 may drive the first light source and the second light source to obtain a hemoglobin index of an object in 1110. Here, the hemoglobin index is obtained by normalizing a hemoglobin signal, and may be related to pressure applied to an object.

The antioxidant sensor 300 or 600 may measure an antioxidant signal according to the hemoglobin index in 1120. For example, the antioxidant sensor 300 or 600 may compare the her globin index with a predetermine threshold value, and may measure an antioxidant signal based on the comparison. In this case, the predetermined threshold value may be preset in consideration of pressure at which an antioxidant signal is saturated and stabilized.

Figure 12:
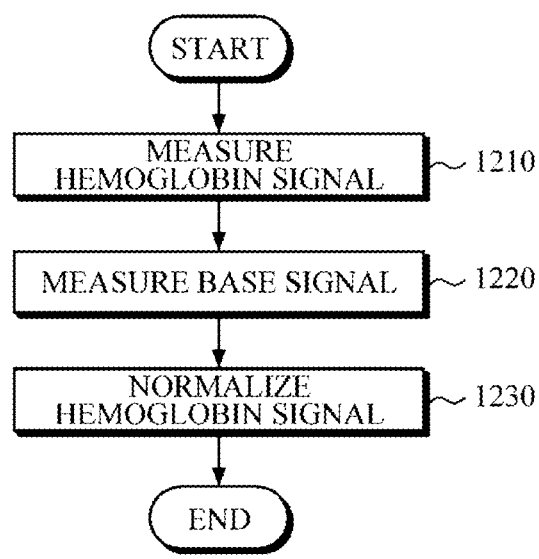
FIG. 12 is a flowchart illustrating an example of a method of obtaining hemoglobin index according to an example embodiment.

FIG. 12 is a flowchart illustrating an example of a hemoglobin index obtaining method according to an example embodiment. The hemoglobin index obtaining method of FIG. 12 may be an example of the obtaining of the hemoglobin index in 1110 of FIG. 11.

Referring to FIGS. 3, 6, and 12, the antioxidant sensor 300 or 600 may drive the first light source to emit light of the first wavelength onto an object, and may measure a hemoglobin signal based on light that is reflected or scattered from the object and received in 1210. In this case, the first wavelength may be a green wavelength included in a wavelength band, in which a hemoglobin signal is measured, i.e., an absorption band of hemoglobin.

The antioxidant sensor 300 or 600 may drive the second light source to emit light of the second wavelength onto an object, and may measure a base signal based on light that is reflected or scattered from the object and received in 1220. In this case, the second wavelength may be a red wavelength.

The antioxidant sensor 300 or 600 may normalize the hemoglobin signal based on the base signal to obtain a hemoglobin index in 1230. In this case, the antioxidant sensor 300 or 600 may normalize the hemoglobin signal by subtracting the base signal from the hemoglobin signal or by dividing the hemoglobin signal by the base signal, and may obtain the normalized hemoglobin signal as the hemoglobin index.

Figure 13:
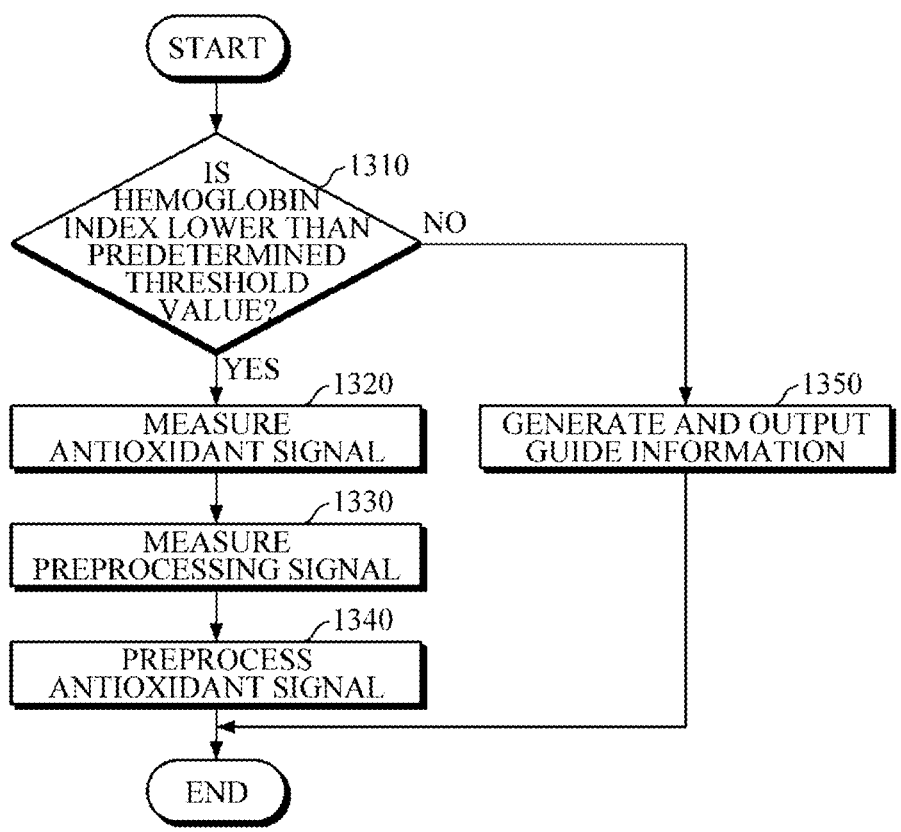
FIG. 13 is a flowchart illustrating an example of a method of obtaining an antioxidant signal according to a hemoglobin index according to an example embodiment.

FIG. 13 is a flowchart illustrating an example of an antioxidant signal obtaining method according to a hemoglobin index according to an example embodiment. The antioxidant signal obtaining method may be an example of the obtaining of the antioxidant signal in 1120 of FIG. 11.

Referring to FIGS. 3, 6, and 13, the antioxidant sensor 300 or 600 may compare a hemoglobin index with a predetermined threshold value in 1310.

In response to a hemoglobin index being lower than a predetermined threshold value, the antioxidant sensor 300 or 600 may drive the third light source to emit light of the third wavelength onto an object, and may measure an antioxidant signal based on light that is reflected or scattered from the object and received in 1320. Here, the third wavelength may be a blue wavelength included in a wavelength band, in which an antioxidant signal is measured, i.e., an absorption band of an antioxidant substance.

In one embodiment, upon obtaining the antioxidant signal of the object, the antioxidant sensor 300 may preprocess the measured antioxidant signal in 1340. For example, the antioxidant sensor 300 may normalize the antioxidant signal by subtracting the hemoglobin signal from the antioxidant signal or by dividing the antioxidant signal by the hemoglobin signal. By normalization, the antioxidant sensor 300 may eliminate an effect of a substance, other than an antioxidant substance, from the measured antioxidant signal.

Further, in another embodiment, upon obtaining the antioxidant signal of the object, the antioxidant sensor 600 may drive the fourth light source to emit light of the fourth wavelength onto an object, and may measure a preprocessing signal based on light that is reflected or scattered from the object and received in 1330. In this case, the fourth wavelength may be a green wavelength or a blue wavelength. Further, the antioxidant sensor 600 may preprocess the antioxidant signal by using the preprocessing signal in 1340. For example, the antioxidant sensor 600 may normalize the antioxidant signal by subtracting the preprocessing signal from the antioxidant signal or by dividing the antioxidant signal by the preprocessing signal. By normalization, the antioxidant sensor 600 may eliminate an effect of a substance, other than an antioxidant substance, from the measured antioxidant signal. In response to a hemoglobin index being greater than or equal to a predetermined threshold value, the antioxidant sensor 600 may generate guide information for guiding a user to increase pressure applied to an object and may provide the guide information to a user through an output device in 1350.

Figure 14:
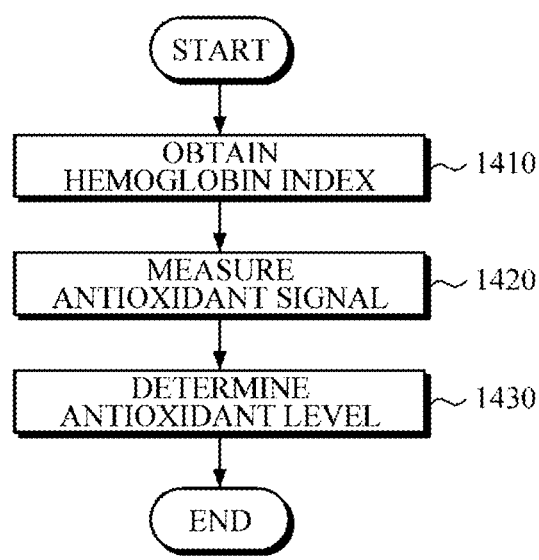
FIG. 14 is a flowchart illustrating an example of a method of obtaining an antioxidant signal according to an example embodiment.

FIG. 14 is a flowchart illustrating an example of an antioxidant signal obtaining method according to an example embodiment. The antioxidant signal obtaining method of FIG. 14 may be performed by the antioxidant sensor 300 or 600 of FIG. 3 or 6. Operations 1410 and 1420 of FIG. 14 may be the same or similar to operations 1110 and 1120 of FIG. 11, such that detailed description thereof will be omitted.

Referring to FIGS. 3, 6, and 14, the antioxidant sensor 300 or 600 may determine an antioxidant level of an object by analyzing the measured antioxidant signal in 1430. For example, the antioxidant sensor 300 or 600 may determine the antioxidant level of the object by using an antioxidant level estimation model. Here, the antioxidant level estimation model defines a relationship between the antioxidant signal and the antioxidant level, and may be pre-generated by regression analysis or machine learning.

In response to an antioxidant level being lower than or equal to a predetermined threshold level, the antioxidant sensor 300 or 600 may generate information recommending to increase the antioxidant level and may provide the information to a user through an output device. For example, in response to an antioxidant level being lower than or equal to a predetermined threshold level, the antioxidant sensor 300 or 600 may generate information indicating, such as "eat more vegetables," "cut down on smoking," "cut down on alcohol consumption," "exercise more," "reduce stress," and the like, and may provide the information to a user through an output device.

Figure 15:
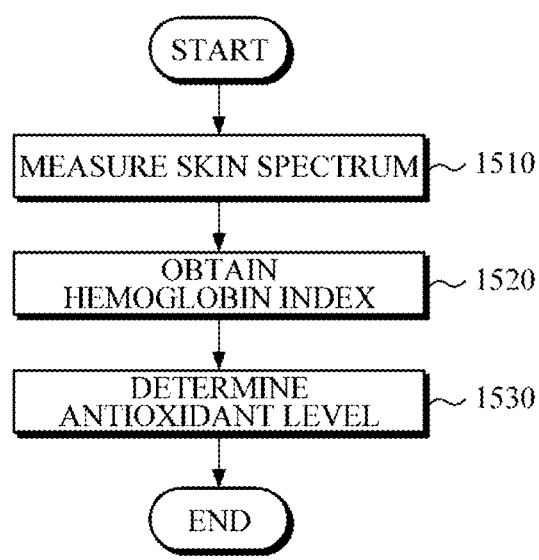
FIG. 15 is a flowchart illustrating an example of a method of determining an antioxidant level according to an example embodiment.

FIG. 15 is a flowchart illustrating an example of an antioxidant level determining method according to an example embodiment. The antioxidant level determining method of FIG. 15 may be performed by the antioxidant sensor 800 of FIG. 8.

Referring to FIGS. 8 and 15, the antioxidant sensor 800 may measure a skin spectrum of an object in 1510.

The antioxidant sensor 800 may obtain a hemoglobin index by analyzing the measured skin spectrum in 1520. Here, the hemoglobin index is obtained by normalizing a hemoglobin signal, and may be related to pressure applied to an object.

The antioxidant sensor 800 may determine an antioxidant level of an object according to a hemoglobin index in 1530. For example, the antioxidant sensor 800 may compare the hemoglobin index with a predetermined threshold value, and may determine an antioxidant level of an object based on the comparison. In this case, the predetermined threshold value may be preset in consideration of pressure at which an antioxidant signal is saturated and is stabilized.

In addition, in response to an antioxidant level being lower than or equal to a predetermined threshold level, the antioxidant sensor 800 may generate information recommending to increase the antioxidant level and may provide the recommendation to a user through an output device. For example, in response to an antioxidant level being lower than or equal to a predetermined threshold level, the antioxidant sensor 800 may generate information indicating, such as "eat more vegetables," "cut down on smoking," "cut down on alcohol consumption," "exercise more," "reduce stress," and the like, and may provide the information to a user through an output device.

Figure 16:
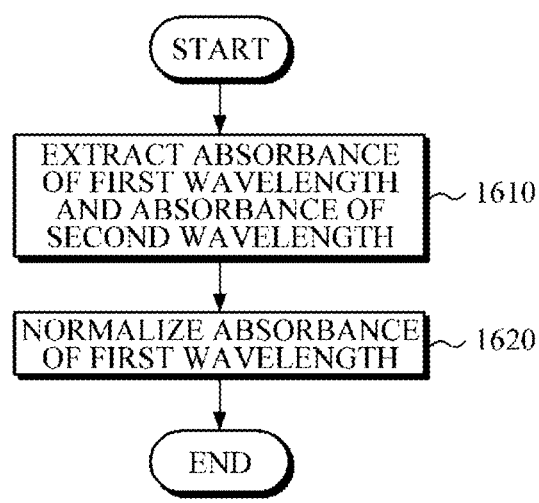
FIG. 16 is a flowchart illustrating an example of a method of obtaining a hemoglobin index according to an example embodiment.

FIG. 16 is a flowchart illustrating an example of a hemoglobin index obtaining method according to an example embodiment. The hemoglobin index obtaining method of FIG. 16 may be an example of the obtaining of the hemoglobin index in 1520 of FIG. 15.

Referring to FIGS. 8 and 16, the antioxidant sensor 800 may extract absorbance of the first wavelength corresponding to a hemoglobin signal, and absorbance of the second wavelength corresponding to a base signal, from the skin spectrum in 1610. In this case, the first wavelength may be a green wavelength, and the second wavelength may be a red wavelength.

The antioxidant sensor 800 may normalize the absorbance of the first wavelength based on the absorbance of the second wavelength, to obtain a hemoglobin index in 1620. For example, the antioxidant sensor 800 may normalize a hemoglobin signal by subtracting the absorbance of the second wavelength from the absorbance of the first wavelength, or by dividing the absorbance of the first wavelength by the absorbance of the second wavelength, and may obtain the normalized hemoglobin signal as a hemoglobin index.

Figure 17:
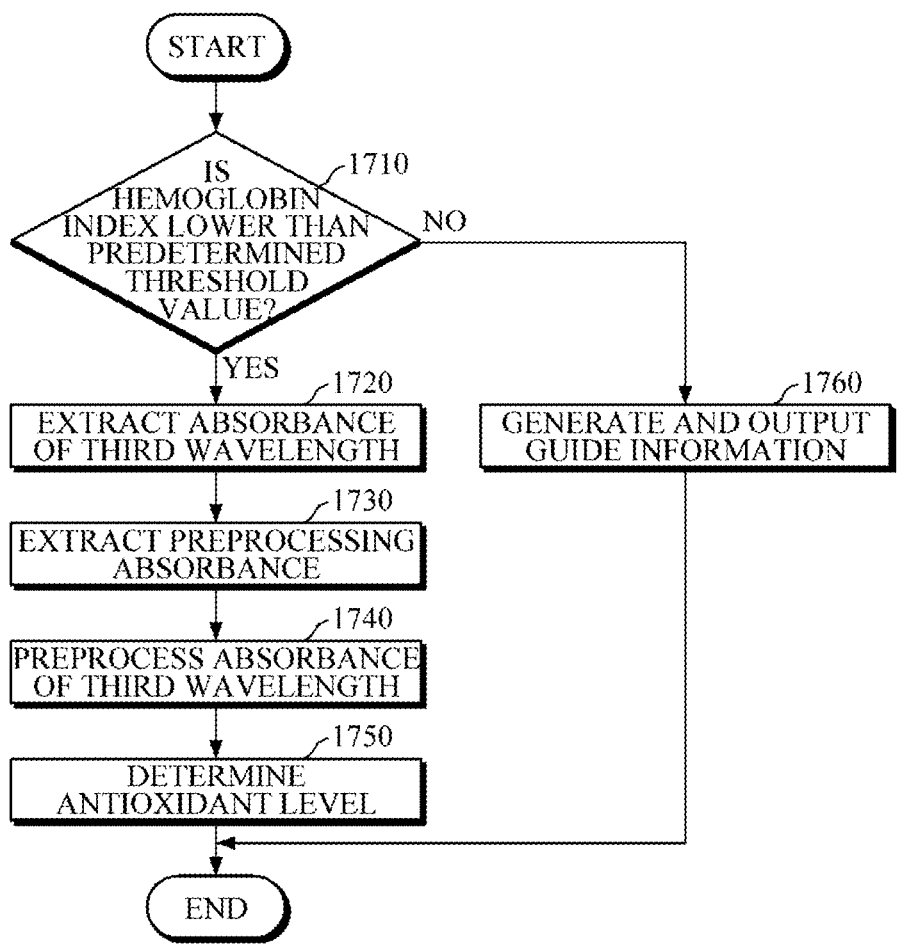
FIG. 17 is a flowchart illustrating an example of a method of determining an antioxidant level according to a hemoglobin index according to an example embodiment.

FIG. 17 is a flowchart illustrating an example of an antioxidant level determining method according to a hemoglobin index according to an example embodiment. The antioxidant level determining method of FIG. 17 may be an example of the determining of the antioxidant level in 1530 of FIG. 15.

Referring to FIGS. 8 and 17, the antioxidant sensor 800 may compare a hemoglobin index with a predetermined threshold value in 1710. In this case, the predetermined threshold value may be preset in consideration of pressure at which an antioxidant signal is saturated and is stabilized.

In response to a hemoglobin index being lower than a predetermined threshold value, the antioxidant sensor 800 may extract absorbance of the third wavelength, corresponding to an antioxidant signal, from the skin spectrum in 1720. In this case, the third wavelength may be a blue wavelength.

The antioxidant sensor 800 may determine an antioxidant level by analyzing the absorbance of the third wavelength in 1750. For example, the antioxidant sensor 800 may determine the antioxidant level of the object by using an antioxidant level estimation model. Here, the antioxidant level estimation model defines a relationship between the antioxidant signal and the antioxidant level, and may be pre-generated by regression analysis or machine learning.

In response to a hemoglobin index being greater than or equal to a predetermined threshold value, the antioxidant sensor 800 may generate guide information for guiding a user to increase pressure applied to an object and may provide the guide information to a user through an output device in 1760.

Further, in one embodiment, upon extracting the absorbance of the third wavelength, the antioxidant sensor 800 may extract preprocessing absorbance of at least one wavelength, corresponding to a preprocessing signal, from the skin spectrum in 1730. In this case, the at least one wavelength, from which the preprocessing absorbance is extracted, may be a blue wavelength or a green wavelength. In addition, the antioxidant sensor 800 may preprocess the absorbance of the third wavelength based on the extracted preprocessing absorbance in 1740. For example, the antioxidant sensor 800 may preprocess the absorbance of the third wavelength by performing normalization or baseline correction of the absorbance of the third wavelength based on the extracted preprocessing absorbance. In this manner, the antioxidant sensor 800 may eliminate an effect of a substance, other than an antioxidant substance, from the absorbance of the third wavelength corresponding to the antioxidant signal.

Figure 18:
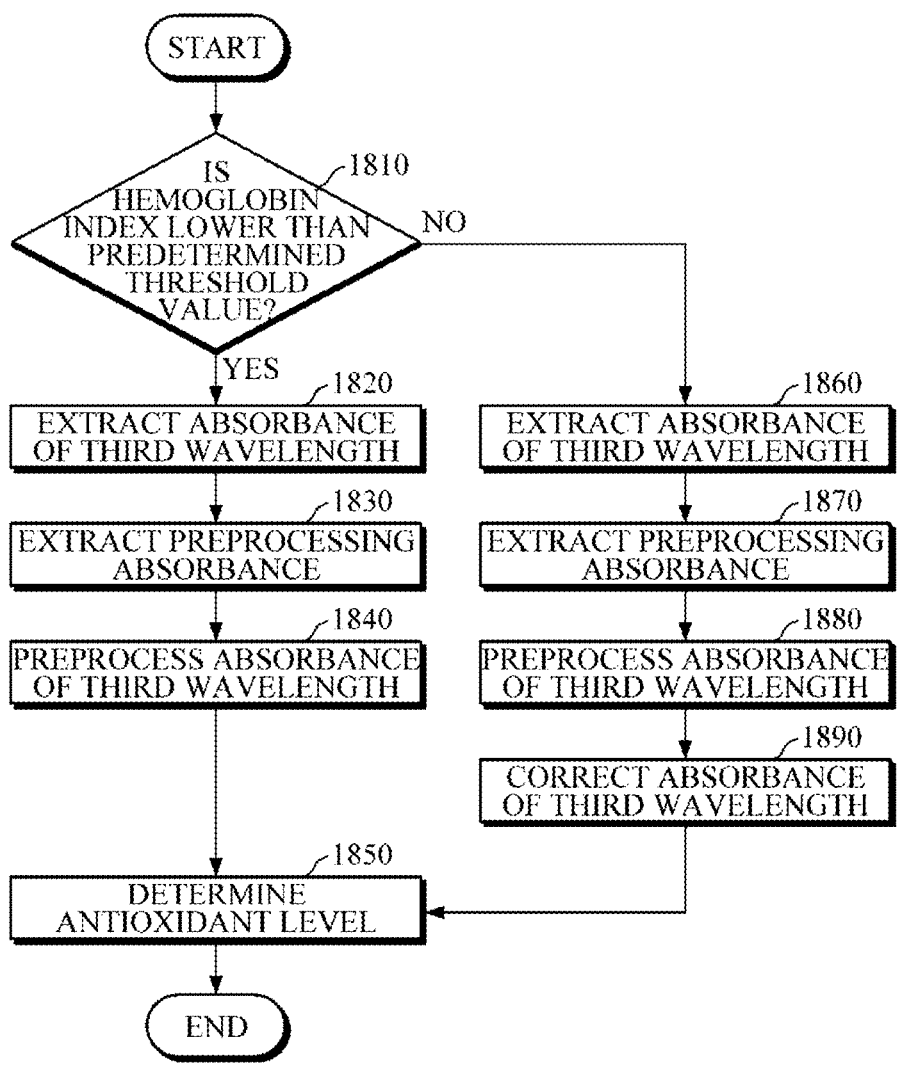
FIG. 18 is a flowchart illustrating an example of a method of determining an antioxidant level according to a hemoglobin index according to an example embodiment.

FIG. 18 is a flowchart illustrating an example of an antioxidant level determining method based on a hemoglobin index according to an example embodiment. The antioxidant level determining method of FIG. 18 may be another optional or additional example of the determining of the antioxidant level in 1530 of FIG. 15. In addition, operations 1810, 1820, 1830, 1840, and 1850 of FIG. 18 may be the same or similar to operations 1710, 1720, 1730, 1740, and 1750 of FIG. 17 respectively, such that detailed description thereof will be omitted.

Referring to FIGS. 8 and 18, in response to a hemoglobin index being greater than or equal to a predetermined threshold value, the antioxidant sensor 800 may extract absorbance of the third wavelength, corresponding to an antioxidant signal, from the skin spectrum in 1860, and may correct the extracted absorbance of the third wavelength according to a hemoglobin index in 1890. For example, the antioxidant sensor 800 may correct the absorbance of the third wavelength by using a correction model. Here, the correction model defines a relationship between the absorbance of the third wavelength and the hemoglobin index, and may be pre-generated by regression analysis or machine learning.

Further, in one embodiment, upon extracting the absorbance of the third wavelength, the antioxidant sensor 800 may extract preprocessing absorbance of at least one wavelength, corresponding to a preprocessing signal, from the skin spectrum in 1870. In this case, the at least one wavelength, from which the preprocessing absorbance is extracted, may be a blue wavelength or a green wavelength. Further, the antioxidant sensor 800 may preprocess the absorbance of the third wavelength based on the extracted preprocessing absorbance in 1880. For example, the antioxidant sensor 800 may preprocess the absorbance of the third wavelength by performing normalization or baseline correction of the absorbance of the third wavelength based on the extracted preprocessing absorbance.

The disclosure can be provided as a computer-readable code written on a computer-readable recording medium. Codes and code segments needed for realizing the disclosure can be easily deduced by computer programmers of ordinary skill in the art. The computer-readable recording medium may be any type of recording device in which data is stored in a computer-readable manner. Examples of the computer-readable recording medium include a read only memory (ROM), a random access memory (RAM), a compact disc (CD)-ROM, a magnetic tape, a floppy disc, an optical disk, and the like. Further, the computer-readable recording medium can be distributed over a plurality of computer systems connected to a network so that a computer-readable recording medium is written thereto and executed therefrom in a decentralized manner.

The disclosure has been described herein with regard to preferred embodiments. However, it will be obvious to those skilled in the art that various modifications can be made without departing from the gist of the invention. Therefore, it is to be understood that that the scope of the invention is not limited to the above-mentioned embodiments, but is intended to include various modifications and equivalents included within the spirit and scope of the appended claims.

What is claimed is:

1. An antioxidant sensor, comprising:
 a first light source configured to emit light having a green wavelength onto an object;
 a second light source configured to emit light having a red wavelength onto the object;
 a third light source configured to emit light having a blue wavelength onto the object;

a light receiver configured to receive light reflected or scattered from the object; and a processor configured to:
drive the first light source and the second light source, and obtain a hemoglobin index by normalizing absorbance of the green wavelength based on absorbance of the red wavelength, and based on the hemoglobin index satisfying a condition, obtain an antioxidant signal of the object by using absorbance of the blue wavelength; and based on the obtained hemoglobin index being lower than a predetermined threshold value, drive the third light source and obtain the antioxidant signal by using the absorbance of the blue wavelength, and wherein the processor is further configured to preprocess the antioxidant signal based on a hemoglobin signal obtained by driving the first light source, wherein preprocessing the antioxidant signal comprises subtracting the hemoglobin signal from the antioxidant signal or dividing the antioxidant signal by the hemoglobin signal.

2. The antioxidant sensor of claim 1, wherein the antioxidant signal is a signal associated with carotenoid.

3. The antioxidant sensor of claim 1, wherein the processor is further configured to:
obtain a hemoglobin signal of the object by driving the first light source;
obtain a base signal by driving the second light source; and
obtain the hemoglobin index by normalizing the hemoglobin signal based on the base signal.

4. The antioxidant sensor of claim 1, wherein the obtained hemoglobin index is based on pressure applied to the object.

5. The antioxidant sensor of claim 1, wherein the processor is further configured to normalize the antioxidant signal by subtracting the hemoglobin signal from the antioxidant signal or by dividing the antioxidant signal by the hemoglobin signal.

6. The antioxidant sensor of claim 1, wherein in response to the obtained hemoglobin index being greater than or equal to a the predetermined threshold value, the processor is further configured to generate guide information indicating to increase pressure applied to the object, and provide the guide information to a user.

7. The antioxidant sensor of claim 1, wherein the light receiver comprises at least one of a photodetector or a spectrometer.

8. The antioxidant sensor of claim 1, further comprising at least one light source configured to emit light having one or more wavelengths to the object,
wherein the processor is further configured to, in response to the obtained hemoglobin index being lower than a the predetermined threshold value, obtain the antioxidant signal by driving the third light source, obtain at least one preprocessing signal by driving the at least one light source, and preprocess the antioxidant signal based on the at least one preprocessing signal.

9. The antioxidant sensor of claim 8, wherein the one or more wavelengths comprise the green wavelength or a wavelength that is the blue wavelength.

10. The antioxidant sensor of claim 1, wherein the processor is further configured to determine an antioxidant level by analyzing the antioxidant signal.

11. The antioxidant sensor of claim 10, wherein in response to the antioxidant level being lower than a predetermined threshold level, the processor is configured to generate recommendation information indicating to increase the antioxidant level and provide the recommendation information to a user.

12. An antioxidant sensor, comprising:
a spectrum obtainer comprising at least one light source and configured to obtain a skin spectrum of an object; and
a processor configured to: extract absorbance of a first wavelength and absorbance of a second wavelength from the skin spectrum;
obtain a hemoglobin index by normalizing the absorbance of the first wavelength based on the absorbance of the second wavelength; and
based on the obtained hemoglobin index being lower than a predetermined threshold value, extract absorbance of a third wavelength from the skin spectrum, and determine an antioxidant level of the object based on to the extracted absorbance of the third wavelength,
wherein the first wavelength, the second wavelength, and the third wavelength are different from each other, and
wherein, the processor is further configured to, based on the obtained hemoglobin index being greater than or equal to the predetermined threshold value, correct the extracted absorbance of the third wavelength based on the hemoglobin index and determine the antioxidant level of the object based on the corrected absorbance of the third wavelength, and wherein
the processor is further configured to extract preprocessing absorbance of at least one wavelength from the skin spectrum, and preprocess the absorbance of the third wavelength based on the preprocessing absorbance,
wherein preprocess the absorbance of the third wavelength comprises subtracting the preprocessing absorbance from the absorbance of the third wavelength or dividing the absorbance of the third wavelength by the preprocessing absorbance.

13. The antioxidant sensor of claim 12, wherein the spectrum obtainer comprises:
a plurality of light sources configured to emit light having different wavelengths onto the object; and
a photodetector configured to receive light reflected or scattered from the object.

14. The antioxidant sensor of claim 12, wherein the spectrum obtainer comprises:
a plurality of light sources configured to emit light having different wavelengths onto the object; and
a spectrometer configured to generate the skin spectrum by separating the light reflected or scattered from the object.

15. The antioxidant sensor of claim 12, wherein the spectrum obtainer comprises:
a light source configured to emit white light onto the object; and
a spectrometer configured to generate the skin spectrum by separating the light reflected or scattered from the object.

16. The antioxidant sensor of claim 12, wherein:
the first wavelength is a green wavelength; and
the second wavelength is a red wavelength.

17. The antioxidant sensor of claim 12, wherein the obtained hemoglobin index is based on pressure applied to the object.

18. The antioxidant sensor of claim 12, wherein:
the third wavelength is a blue wavelength; and
the at least one wavelength is the blue wavelength or a green wavelength.

19. The antioxidant sensor of claim 12, wherein, the processor is further configured to, in response to the obtained hemoglobin index being greater than or equal to the predetermined threshold value, generate guide information indicating to increase pressure applied to the object, and provide the guide information to a user.

20. The antioxidant sensor of claim 12, wherein the processor is further configured to correct the absorbance of the third wavelength by using a correction model which defines a relationship between the hemoglobin index and the absorbance of the third wavelength.

21. The antioxidant sensor of claim 12, wherein in response to the antioxidant level being lower than a predetermined threshold level, the processor is configured to generate recommendation information indicating to increase the antioxidant level and provide the recommendation information to a user.

\* \* \* \* \*